US 9,855,107 B2

(12) United States Patent
Labonville et al.

(10) Patent No.: US 9,855,107 B2
(45) Date of Patent: Jan. 2, 2018

(54) MEDICAL ROBOTIC SYSTEM WITH REMOTE CURRENT CONTROLLER FOR CONTROLLING A PLURALITY OF DISTALLY HOUSED MOTORS

(71) Applicant: INTUITIVE SURGICAL OPERATIONS, INC., Sunnyvale, CA (US)

(72) Inventors: Gerard J. Labonville, San Jose, CA (US); Alan S. Bradley, Alameda, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 14/902,825

(22) PCT Filed: Aug. 8, 2014

(86) PCT No.: PCT/US2014/050347
§ 371 (c)(1),
(2) Date: Jan. 4, 2016

(87) PCT Pub. No.: WO2015/021384
PCT Pub. Date: Feb. 12, 2015

(65) Prior Publication Data
US 2016/0166339 A1    Jun. 16, 2016

Related U.S. Application Data

(60) Provisional application No. 61/864,061, filed on Aug. 9, 2013.

(51) Int. Cl.
*G05B 19/19* (2006.01)
*A61B 34/30* (2016.01)
(Continued)

(52) U.S. Cl.
CPC .............. *A61B 34/30* (2016.02); *A61B 34/37* (2016.02); *A61B 34/70* (2016.02); *B25J 9/161* (2013.01);
(Continued)

(58) Field of Classification Search
CPC ... B25J 5/00; B25J 19/18; B25J 19/22; G05B 19/04
(Continued)

(56) References Cited

U.S. PATENT DOCUMENTS 5,757,634 A    5/1998  Ferens
6,344,720 B1   2/2002  Koski et al.
(Continued)

FOREIGN PATENT DOCUMENTS

WO    WO-2012106375 A1    8/2012

OTHER PUBLICATIONS

International Search Report and Written Opinion for Application No. PCT/US14/50347, dated Nov. 12, 2014, 9 pages.
(Continued)

*Primary Examiner* — Antony M Paul (57) ABSTRACT

A medical robotic system includes a manipulator having links that form housings which are movable by motor actuated joints. Motors for actuating the joints and sensors for sensing states of the motors are housed in one or more distal housings formed from corresponding links or other structure(s) of the manipulator. A position controller is housed in a proximal housing and provides current commands for the motors to a remote current controller that is housed in an intermediate housing and generates drive signals for the motors by using the provided current commands and sensed states of the motors.

20 Claims, 8 Drawing Sheets

(51) Int. Cl.
    B25J 9/16       (2006.01)
    A61B 34/37      (2016.01)
    A61B 34/00      (2016.01)
    A61B 17/00      (2006.01)
    A61B 34/20      (2016.01)

(52) U.S. Cl.
    CPC ........... *A61B 2017/00477* (2013.01); *A61B 2034/2059* (2016.02); *A61B 2034/306* (2016.02); *G05B 2219/45117* (2013.01)

(58) Field of Classification Search
    USPC ......... 318/560, 561, 568.11, 568.12, 568.16, 318/568.17, 568.18, 568.2, 568.21; 700/13, 69, 245, 248, 249; 901/3, 4, 5, 9, 901/14, 19, 23, 30; 606/1
    See application file for complete search history.

(56) References Cited

U.S. PATENT DOCUMENTS

| | | | |
|---|---|---|---|
| 6,522,096 B1 | 2/2003 | Roth | |
| 6,999,851 B2 * | 2/2006 | Kato | G06N 3/008 318/568.1 |
| 7,710,061 B2 | 5/2010 | Niemeyer et al. | |
| 7,756,036 B2 | 7/2010 | Druke et al. | |
| 7,757,028 B2 | 7/2010 | Druke et al. | |
| 7,979,157 B2 | 7/2011 | Anvari | |
| 8,054,752 B2 | 11/2011 | Druke et al. | |
| 2004/0103740 A1 | 6/2004 | Townsend et al. | |
| 2006/0087746 A1 | 4/2006 | Lipow | |
| 2007/0137372 A1 | 6/2007 | Devengenzo et al. | |
| 2010/0101346 A1 * | 4/2010 | Johnson | B25J 9/1641 74/405 |
| 2010/0274087 A1 | 10/2010 | Diolaiti et al. | |
| 2011/0118874 A1 | 5/2011 | Tanabe et al. | |
| 2011/0282491 A1 | 11/2011 | Prisco et al. | |
| 2012/0215358 A1 * | 8/2012 | Gettings | B25J 5/005 700/259 |

OTHER PUBLICATIONS

Richard A. Guinee, "Mathematical Modeling and Simulation of a PWM Inverter Controlled Brushless Motor Drive System from Principles for Electric Vehicle Propulsion Systems", Electric Vehicles—Modeling and Simulations, edited by Dr. Seref Soylu, Publisher InTech, published online Sep. 12, 2011.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP14834711.5, dated Feb. 14, 2017, 9 pages.

* cited by examiner fig.1 fig.2 fig.3 fig.4 fig.5 fig.6 fig.7 fig.8 fig.9

MEDICAL ROBOTIC SYSTEM WITH REMOTE CURRENT CONTROLLER FOR CONTROLLING A PLURALITY OF DISTALLY HOUSED MOTORS

RELATED APPLICATIONS

This application is the U.S. national phase of International Application No. PCT/US2014/050347, filed Aug. 8, 2014, which designated the U.S. and claims priority to U.S. provisional patent application 61/864,061, filed on Aug. 9, 2013, the contents of each of which are incorporated herein by reference.

FIELD OF THE INVENTION

The present invention generally relates to medical robotic systems and in particular, to a medical robotic system with remote current controller for controlling a plurality of distally housed motors.

BACKGROUND

Medical robotic systems such as systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms with slave manipulators that move attached medical devices, such as an image capturing device and Intuitive Surgical's proprietary EndoWrist® articulating surgical instruments, in response to movement of associated master controllers operated by a surgeon as the surgeon is viewing images on a display screen of a surgical site which have been captured by the image capturing device.

A plurality of motors is provided in the medical robotic system to actuate corresponding degrees of freedom of the slave manipulators and their attached medical devices. As an example, U.S. Pat. No. 6,424,885 entitled "Camera Referenced Control in a Minimally Invasive Surgical Apparatus," which is incorporated herein by reference, describes a master/slave control system for controlling the position and orientation of an attached medical device by moving its manipulator in response to movement of an associated master controller.

In practice, the plurality of motors may be distributed at various locations within the robotic arm so as to be near joints or other mechanical elements that they respectively actuate. For control purposes, sensors which sense states of the motors are generally located near their respective motors. For simplicity in implementation, it may be advantageous to locate the motor's current controller within close proximity to the motor's sensors. In situations where the motor and its sensors are disposed in a small housing, however, trying to place the current controller in the same housing as its motor may result in space and/or heating problems.

SUMMARY

Accordingly, one object of one or more aspects of the present invention is an arrangement of motor control systems which meet performance and stability requirements while overcoming space restrictions in a medical robotic system.

Another object of one or more aspects of the present invention is an arrangement of motor control systems which meet performance and stability requirements while avoiding excessive heat problems in a medical robotic system.

These and additional objects are accomplished by the various aspects of the present invention, wherein briefly stated, one aspect is a distributed control system for controlling a plurality of motors to actuate movement of a robotically manipulated device, the distributed control system comprising: a plurality of sensors coupled to the plurality of motors for sensing states of the plurality of motors, wherein the plurality of sensors and the plurality of motors are disposed in one or more distal housings; and a remote current controller adapted to receive current commands indicative of commanded positions of the plurality of motors from a position controller, receive information of the sensed states of the plurality of motors, generate individual motor driving signals for the plurality of motors by using the received current commands and the received information of the sensed states of the plurality of motors, and transmit the individual motor driving signals to the plurality of motors; wherein the position controller is disposed in a proximal housing, and wherein the remote current controller is disposed in an intermediate housing that is between the proximal housing and the one or more distal housings.

Another aspect is a robotic system comprising: one or more distal housings in which a plurality of motors and a plurality of sensors are housed, wherein the plurality of sensors is coupled to the plurality of motors for sensing states of the plurality of motors; a proximal housing in which a position controller is housed, wherein the position controller generates current commands indicative of commanded positions of the plurality of motors; and an intermediate housing in which a remote current controller is housed, wherein the intermediate housing is between the proximal housing and the one or more distal housings, and wherein the remote current controller is adapted to: receive the current commands, receive information of the sensed states of the plurality of motors, generate individual motor driving signals for the plurality of motors using the received current commands and the received information of the sensed states of the plurality of motors, and transmit the individual motor driving signals to the plurality of motors over individual signal lines.

Additional objects, features and advantages of the various aspects of the present invention will become apparent from the following description, which should be taken in conjunction with the accompanying drawings.

DESCRIPTION

Figure 1:
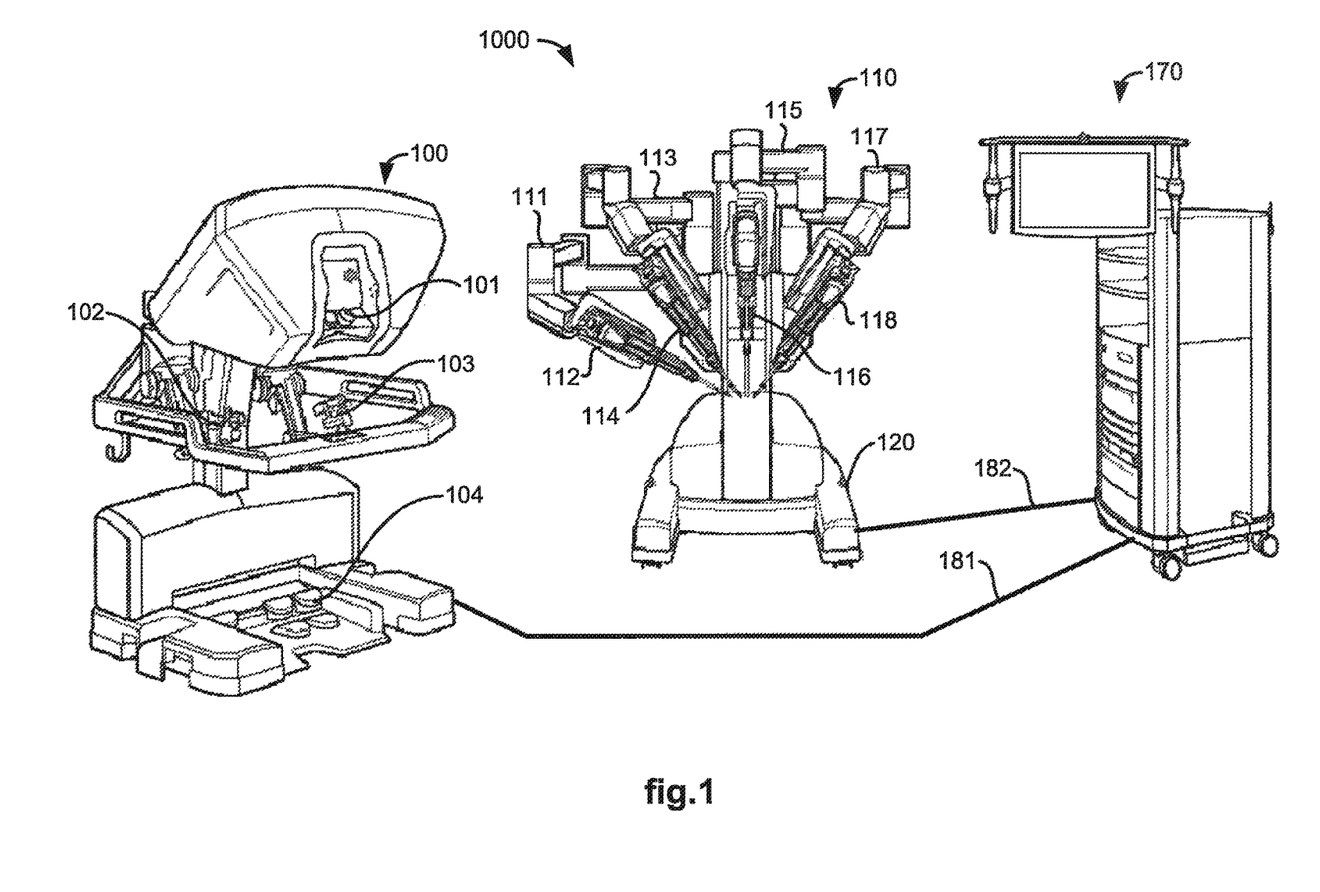
FIG. 1 illustrates a perspective view of a medical robotic system.

FIG. 1 illustrates, as an example, a perspective view of a medical robotic system 1000 that includes a surgeon console 100, a patient side cart 110, and a vision cart 170, which communicate with one another through cables 181, 182. The surgeon console 100 includes a stereo viewer 101, hand-manipulatable master controllers 102, 103, and at least one foot pedal 104. The patient side cart 110 includes a base 120 and robotic arms 111, 113, 115, and 117 that are adapted to hold, move and manipulate removably attachable medical devices.

In the example of FIG. 1, the robotic arms 111, 113, and 117 hold surgical instruments 112, 114, and 118 and the robotic arm 115 holds a stereoscopic endoscope 116. Alternatively, each of the robotic arms 111, 113, 115, and 117 may hold a different type of medical device or hold no medical device at all while a medical procedure is being performed. As an example, a second image capturing device such as an ultrasound transducer may replace the surgical instrument 112 being held by the robotic arm 111. As another example, robotic arm 111 may be left unused with no medical device attached to it during all or a part of a surgical procedure.

The stereoscopic endoscope 116 captures stereo images which are continuously transmitted as a video stream to the vision cart 170. The vision cart 170 processes each pair of stereo images as it is received and transmits the processed pair of stereo images to the surgeon console 100 for display on the stereo viewer 101 in substantially real-time. Thus, a surgeon may view stereo images of a work site which have been captured by the stereoscopic endoscope 116 while telerobotically manipulating the surgical instruments 112, 114, and 118 and/or the stereoscopic endoscope 116 by manipulating associated ones of the master controllers 102, 103 and/or foot pedal 104. Master/slave control systems are provided in the medical robotic system 1000 to facilitate such telerobotic manipulations.

The robotic arms 111, 113, 115, and 117 may be individually moved up or down in a vertical direction (e.g., towards the ceiling or towards the floor) relative to the base 120. Each of the robotic arms 111, 113, 115, and 117 preferably includes a manipulator and a set-up arm. The manipulator is adapted to hold a medical device and manipulate it about a pivot point. The set-up arm is adapted to horizontally translate the manipulator in space so that the manipulator's held medical device and the medical device's pivot point are also horizontally translated in space.

Figure 2:
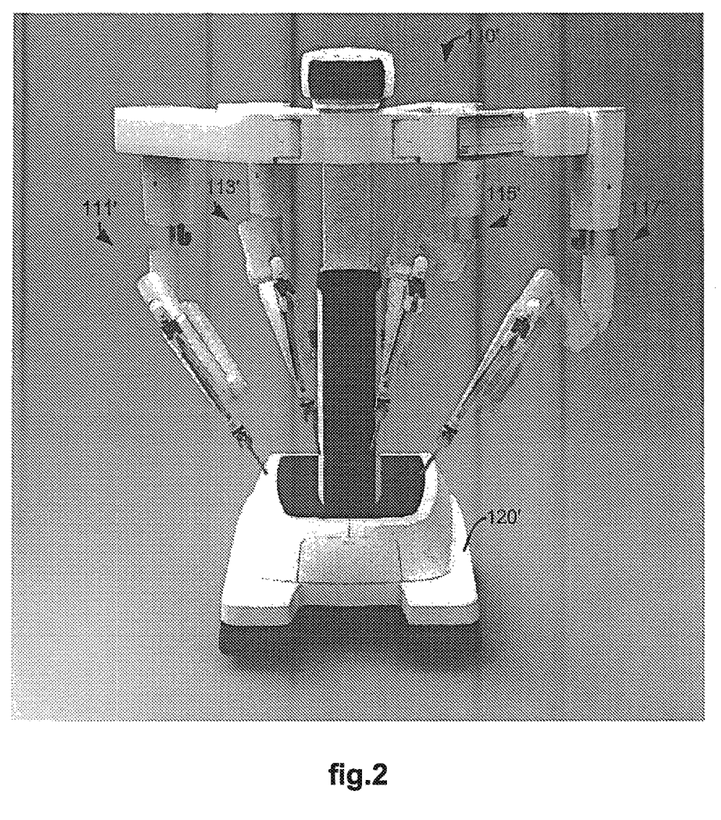
FIG. 2 illustrates an alternative patient side cart usable in the medical robotic system.

FIG. 2 illustrates, as an example, an alternative and preferred patient side cart 110' that has robotic arms 111', 113', 115', and 117' which are similarly constructed to each other so that each arm may hold and manipulate any one of the surgical instruments shown. Each of the arms 111', 113', 115', and 117' is also generally lighter and dimensionally smaller than its counterpart arm of the patient side cart 110. Also different than their counterparts of the patient side cart 110, the robotic arms 111', 113', 115', and 117' may be moved in unison up or down in the vertical direction relative to their base 120'.

Figure 3:
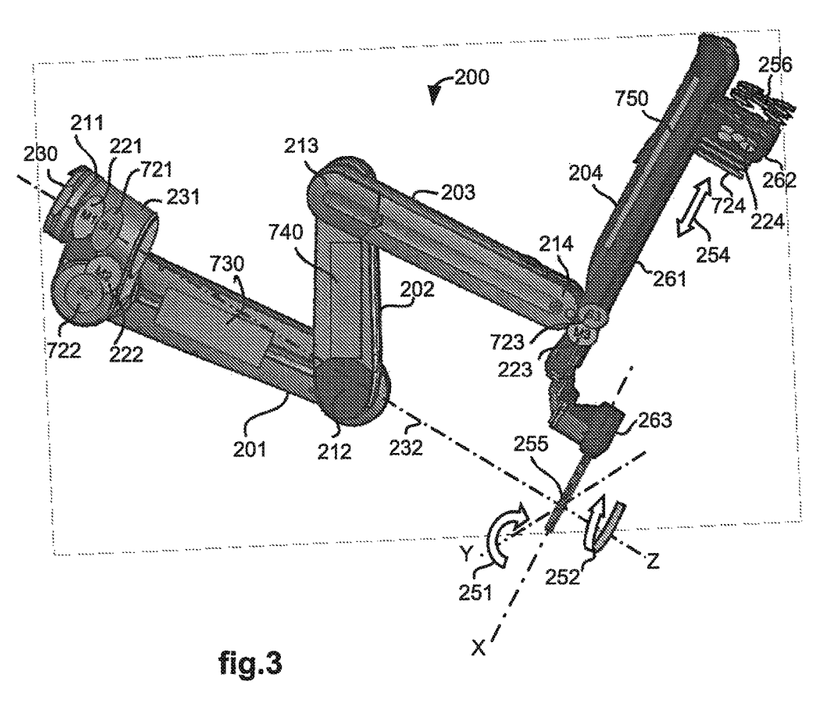
FIG. 3 illustrates a perspective view of a manipulator included as part of a robotic arm in a medical robotic system.
Figure 4:
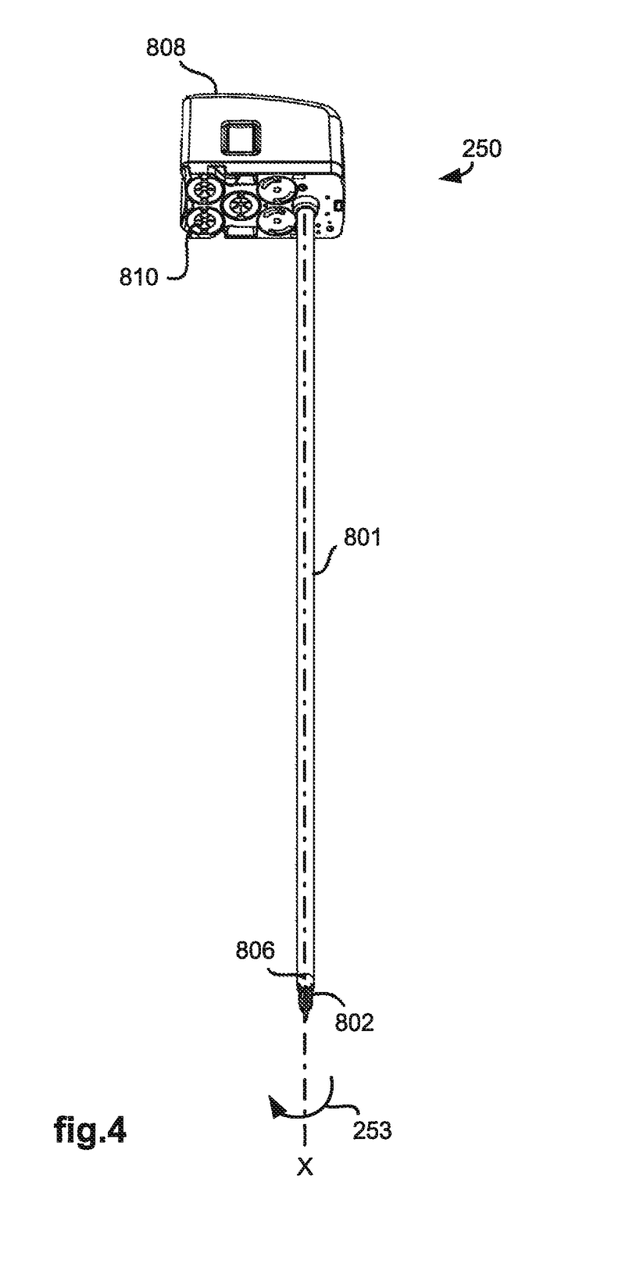
FIG. 4 illustrates a perspective view of an attachable instrument includable in a medical robotic system.

FIG. 3 illustrates, as an example, a manipulator 200 that is representative of the manipulators of the robotic arms 111', 113', 115', and 117'. The manipulator 200 is adapted to hold a removably attachable medical device 250 (not shown). In this example, the medical device 250 may be an image capturing device, such as a stereoscopic endoscope or an ultrasonic transducer. Alternatively, the medical device 250 may be a medical implement, such as a surgical instrument or tool. An exemplary medical device 250 is shown in FIG. 4. The manipulator 200 is further adapted to move the medical device 250 in pitch, yaw, roll, and in/out (I/O) degrees of freedom relative to orthogonal X, Y, and Z axes which intersect at a pivot point 255. When the medical device 250 includes a wrist mechanism for controllably orienting a distal end of the medical device 250 and/or an actuatable end effector at the distal end of the medical device 250, the manipulator 200 is further adapted to actuate degrees of freedom of the wrist mechanism and/or end effector of the medical device 250.

The manipulator 200 comprises a plurality of connected links and joints. Link 231 is coupled to a proximal end 230 of a set-up arm at joint 211. The link 231 is also attached to a link 201 so that a longitudinal axis 232 of link 231 coincides with the Z axis. Links 201, 202, 203, and 204 are coupled together at joints 212, 213, and 214 as shown.

A yaw motor 221 is housed in the link 231 so that the link 231 rotates about its longitudinal axis 232 at the joint 211 when the motor 221 is actuated. As a consequence of the link 231 rotating about its longitudinal axis, a cannula 263, through which the medical device 250 is insertable, rotates in a yaw angle 252 about the Z axis at the pivot point 255.

A pitch motor 222 is housed in the link 201 so that when the motor 222 is actuated, it causes link 202 to rotate at the joint 212 relative to link 201, the link 202 to rotate at the joint 213 relative to link 203, and the link 204 to rotate at the joint 214 relative to the link 203, using conventional internal mechanical assemblies such as those employing cables and/or flat metal bands. The links 201, 202, 203, and 204 are constrained to move in unison so that, when the motor 222 is actuated, it results in the cannula 263 being rotated in a pitch angle 251 about the Y axis at the pivot point 255.

An in/out (I/O) motor 223 is housed in the link 204 so that when the motor 223 is actuated, it causes a carriage 262 to move along a rail 261. The rail is provided in or on the link 204 so as to extend parallel to a longitudinal axis of the link 204. The cannula 263 is attached to the distal end of the link 204. When the medical device 250 is inserted into the cannula 263 and attached to the carriage 262, actuation of the motor 223 results in the carriage 262 moving in an in/out direction (as indicated by arrow 254) and a shaft 801 of an attached medical device 250 moving along the X axis when the shaft 801 is inserted in and guided by the cannula 263. A plurality of motors 224 is housed in the carriage 262 to actuate corresponding degrees of freedom of the medical device 250. As an example, a first motor of the plurality of motors 224 is provided to actuate gearing which when actuated causes the medical device 250 to rotate (as indicated by arrow 253 in FIG. 4) about its longitudinal axis. As shown in FIGS. 3 and 4, the X axis coincides with the longitudinal axis of the medical device 250, the Z axis coincides with the longitudinal axis 232 of the link 231, and the Y axis is orthogonal to the X and Z axes. As another example, when the medical device 250 has a wrist joint 806 with two degrees of freedom (such as orienting the distal end of the medical device 250 in a pitch direction and in a yaw direction), second and third motors of the plurality of motors 224 are provided to respectively actuate the two degrees of freedom. As yet another example, when the medical device 250 has an actuatable end effector 802 with one degree of freedom (such as the opening and closing of a pair of jaws), a fourth motor of the plurality of motors 224 is provided to actuate the degree of freedom.

An example of the medical device 250 is shown in FIG. 4, wherein the medical device 250 is a surgical instrument that has an interface 808 for attachment to the carriage 262, a shaft 801 which is insertable into the cannula 263, a wrist mechanism 806, and an end effector 802. As seen from the underside of the interface 808, mechanical interfaces 810 are provided on the interface 808 to mechanically couple the plurality of motors 224 of the manipulator 200, when the medical device 250 is attached to the carriage 262, to mechanical elements in the medical device 250 which translate motions 256 of the motors 224 to actuate the corresponding degrees of freedom of the medical device 250.

Figure 5:
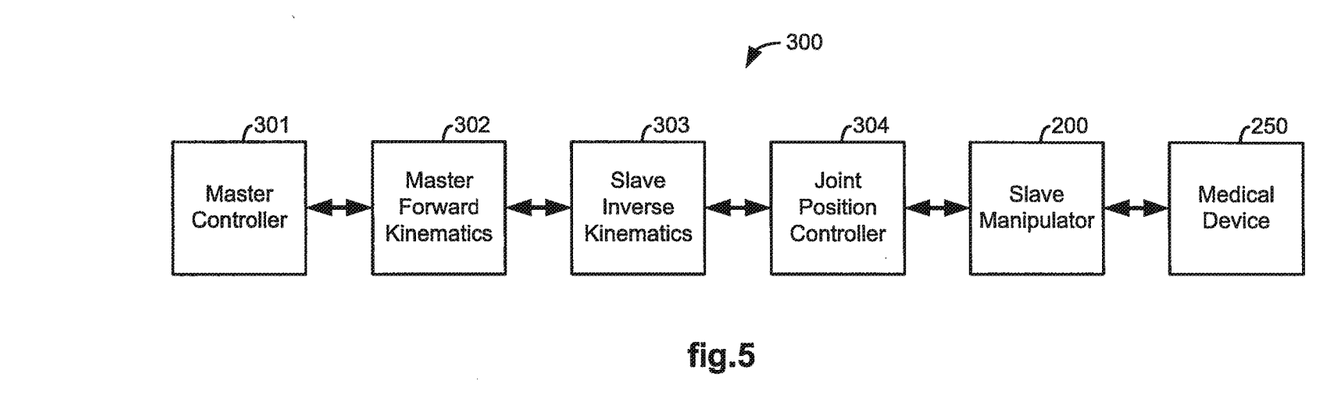
FIG. 5 illustrates a block diagram of a master/slave control system included in a medical robotic system.

FIG. 5 illustrates, as an example, a block diagram of a master/slave control system 300 in which an operator manipulates a master controller 301 (such as one of the master controllers 102, 103) to command movement of the medical device 250 by the slave manipulator 200 to a desired state. Similar master/slave control systems may be provided in the medical robotic system 1000 for controlling other medical devices being held by other slave manipulators in response to operator manipulation of master controllers which are associated with those medical devices at the time. The master controller 301 provides information of its joint states to a master forward kinematics unit 302. The master forward kinematics block 302 maps the sensed states of joints of the master controller 301 to a desired state of the medical device 250. A slave inverse kinematics block 303 then maps the desired state of the medical device 250 to joint positions of the slave manipulator 200 and/or medical device 250 which would result in the medical device 250 being at the desired state. A joint position controller 304 then converts the desired joint positions $\hat{\theta}_C$ of the slave manipulator 200 and medical device 250 to current commands $\hat{I}_C$ for driving motors in the slave manipulator 200 to actuate their respective joints to their desired joint positions. Feedback is provided along the way to facilitate smooth control of the medical device 250.

Figure 6:
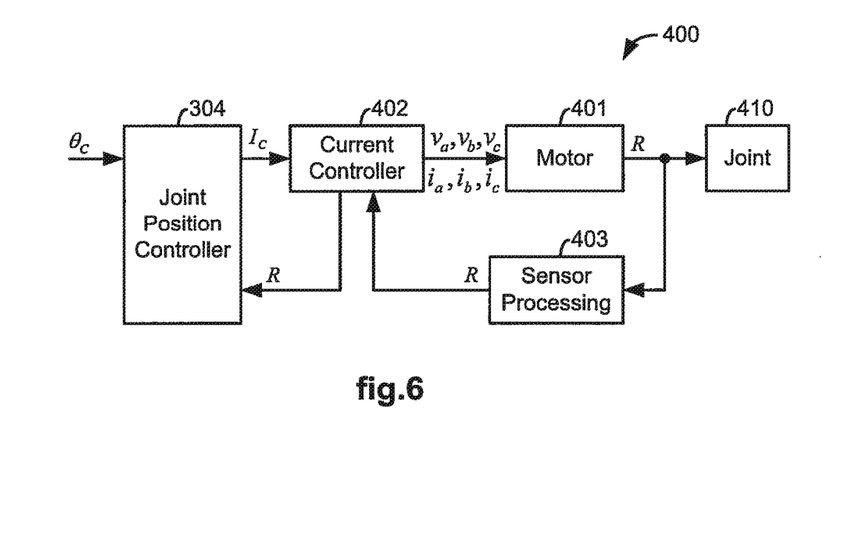
FIG. 6 illustrates a block diagram of a joint control system included in a medical robotic system.

FIG. 6 illustrates, as an example, a block diagram of a joint control system 400 that is used to control a motor 401 that actuates a joint 410 of the slave manipulator 200 or medical device 250. Similar joint control systems may be provided in the medical robotic system 1000 for controlling other motors which actuate other joints of the slave manipulator 200 or medical device 250. In the present example, the motor 401 is preferably a three-phase brushless Direct Current (DC) motor which is controlled by a current controller 402. The current controller 402 receives a current command $I_C$ from the joint position controller 304 and generates pulse-width modulated voltage signals $v_a$, $v_b$, and $v_c$ which it provides to respective motor windings of the three-phase brushless DC motor 401. Sensor Processing Unit 403 includes one or more sensors, such as Hall effect sensors and/or a rotary encoder, which sense the rotor angle R of the motor 401 and feed information of the sensed rotor angle R back to the current controller 402. The sensed rotor angle R may also be fed back directly to the joint position controller 304 or indirectly, as shown, through the current controller 402. The current controller 402 generates the pulse-width modulated voltage signals $v_a$, $v_b$, and $v_c$ in response to the current command $I_c$ in a conventional manner by using the sensed rotor angle R feedback for phase adjustments and by using internally sensed output voltages $v_a$, $v_b$, and $v_c$ and/or currents $i_a$, $i_b$, and $i_c$ (i.e., the currents flowing into the motor windings) for current control feedback.

Figure 7:
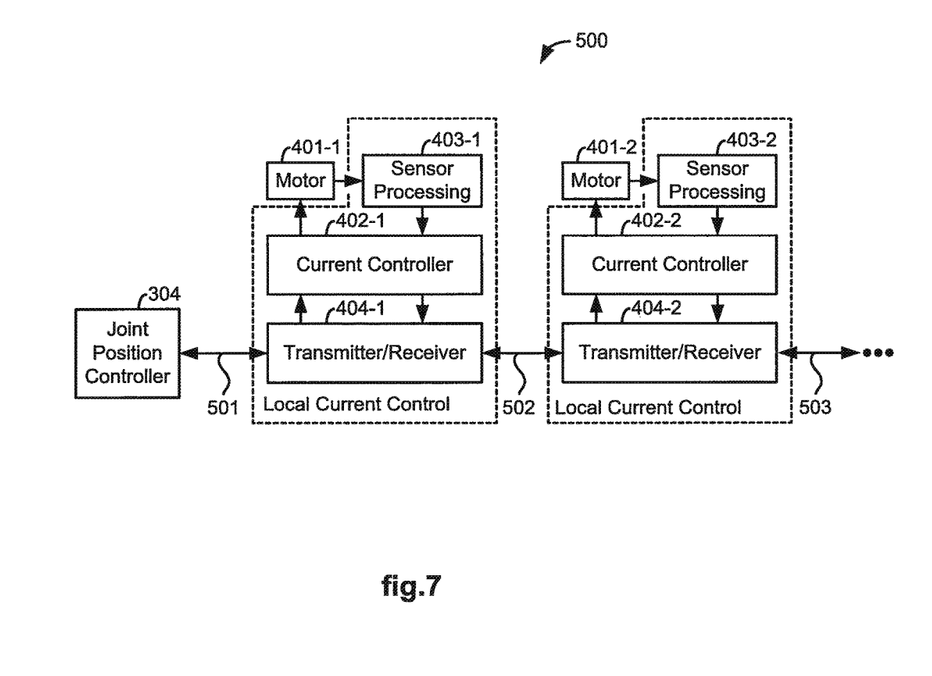
FIG. 7 illustrates a block diagram of a first arrangement of networked motor control systems included in a medical robotic system.

FIG. 7 illustrates, as an example, a block diagram of a first arrangement 500 of networked motor control systems which may be included in the medical robotic system 1000 to control movement of one of its robotic arms. In this arrangement, the current controllers (e.g., 402-1, 402-2) are preferably local or at least proximate to their respective motors (e.g., 401-1, 401-2) in the manipulator 200. Each of the current controllers (e.g., 402-1, 402-2) has a corresponding transmitter/receiver (e.g., 404-1, 404-2). The transmitters/receivers (e.g., 404-1, 404-2) are networked to the joint position controller 304 in a daisy chain in this example. Thus, the transmitter/receiver 404-1 for the current controller 402-1 communicates with the joint position controller 304 via communication link 501, the transmitter/receiver 404-2 for the current controller 402-2 communicates with the transmitter/receiver 404-1 for the current controller 402-1 via communication link 502, and a next transmitter/receiver for the next current controller communicates with transmitter/receiver 404-2 for the current controller 402-2 via link 503, and so on. Other communication schemes are also contemplated to be usable, such as star patterns and a hybrid combination of star and daisy chain links.

Thus, in such a daisy chain arrangement, each transmitter/receiver (e.g., 404-1, 404-2) in the daisy chain receives a packet of information from an adjacent upstream/downstream transmitter/receiver and checks a destination field in the packet of information to determine if the packet is intended for its current controller. The transmitter/receiver then either passes the received packet of information to its current controller if the destination field indicates that its current controller is the destination or it passes the received packet of information to an adjacent downstream/upstream transmitter/receiver if the destination field indicates that its current controller is not the destination (i.e., the destination is further downstream if the packet was received from an adjacent upstream transmitter/receiver or the destination is further upstream if the packet was received from an adjacent downstream transmitter/receiver).

Although only two motors 401-1, 401-2 are shown, it is to be appreciated that all current controllers for all motors in the manipulator 200 may be networked in this fashion. As to be understood herein, the term "local" means the current controller is within the same housing as its motor and sensor processing unit. As an example of a local current controller, in FIG. 3, the current controller for motor 222 (and its transmitter/receiver) is on printed circuit board 730 which is housed in link 201 along with the motor 222. Therefore, the current controller on printed circuit board 730 is local to its motor 222 since the link 201 serves as a housing that encloses the printed circuit board 730 and the motor 222.

Figure 8:
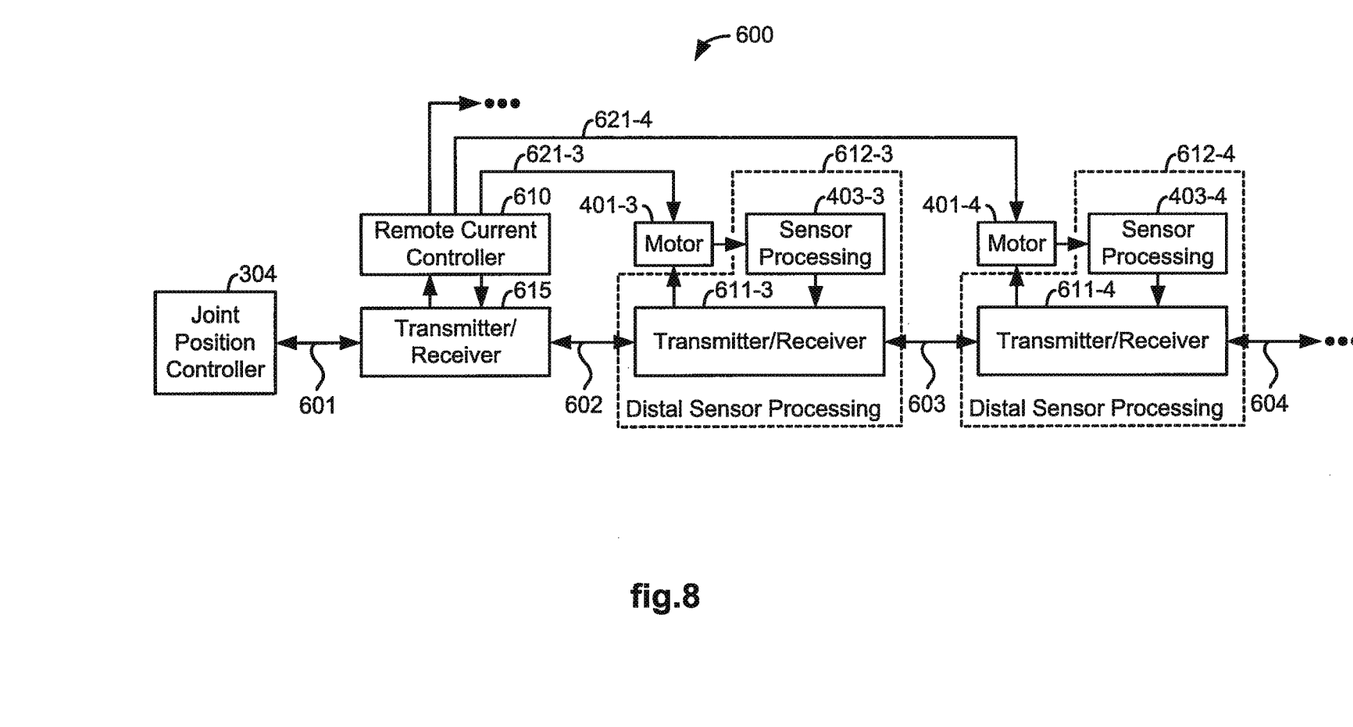
FIG. 8 illustrates a block diagram of a second arrangement of networked motor control systems included in a medical robotic system.

FIG. 8 illustrates, as an example, a block diagram of a second arrangement 600 of networked motor control systems which may be included in the medical robotic system 1000. In this arrangement, a single current controller 610 is remote from the motors (e.g., 401-3, 401-4) which it provides pulse-width modulated current signals for in the manipulator 200. As to be understood herein, the term "remote" means the current controller is in a different housing than the motors which it provides pulse-width modulated current signals for. As an example of a remote current controller, in FIG. 3, a remote current controller (and its transmitter/receiver) is provided on printed circuit board 740 which is housed in link 202, whereas the motors 223, 224, which it provides pulse-width modulated current signals for, are housed respectively in link 204 and the carriage 262. Thus, the remote current controller on printed circuit board 740 is remote from the motors which it provides pulse-width modulated currents for since it is in a different housing than the motors. In particular, the motors are disposed in housings which are distal to that of the housing for the remote current controller.

Sensor processing units (e.g., 403-3, 403-4) are provided to sense states of the motors (e.g., 401-3, 401-4). The remote current controller 610 and the sensor processing units (e.g., 403-3, 403-4) are networked with the transmitter/receiver 615 of the remote current controller 610 in a daisy chain. In order for the sensor processing units (e.g., 403-3, 403-4) to communicate on the daisy chain network, a transmitter/receiver (e.g. 611-3, 611-4) is provided for each of the sensor processing units (e.g., 403-3, 403-4) to form a distal sensor processing unit (e.g., 612-3, 612-4). Thus, the transmitter/receiver 615 of the remote current controller 610 communicates with the joint position controller 304 via communication link 601, the transmitter/receiver 611-3 for sensor processing unit 403-3 communicates with the transmitter/receiver 615 of the current controller 610 via communication link 602, the transmitter/receiver 611-4 for sensor processing unit 403-4 communicates with the transmitter/receiver 611-3 for sensor processing unit 403-3 via communication link 603, and a next transmitter/receiver for a next sensor processing unit in the daisy chain communicates with the transmitter/receiver 611-4 for sensor processing unit 403-4 via communication link 604, and so on.

Information is preferably communicated over the daisy chain network in packets using a packet-switching protocol. As an example of such a packet-switching protocol, see U.S. Pat. No. 8,054,752 entitled "Synchronous Data Communication," which is incorporated herein by reference. In order to associate current commands with their intended motors in communications from the joint position controller 304 to the remote current controller 610, the current command is provided in a data field in a packet and the motor which it is intended for is identified in a destination field in the packet. Likewise, in order to associate sensor information with their respective motors in communications from the distal sensor processing units (e.g., 612-3, 612-4) to the remote current controller 610, the sensor information is provided in a data field in a packet and the motor which it applies to is identified in a source field in the packet. In this latter case, the remote current controller 610 is identified in the destination field. Communication links (e.g., 602, 603, and 604) between the transmitter/receiver 615 of the remote current controller 610 and the distal sensor processing units (e.g., 612-3, 612-4) are preferably high-speed communication links to ensure system performance and stability requirements.

Two control loops are definable in the second arrangement 600 of networked motor control systems. A "position loop" is defined by the process cycle of the joint position controller 304 and a "current loop" is defined by the process cycle of the remote current controller 610. In one embodiment, the "position loop" is approximately a 750 μs (microsecond) loop and the "current loop" is approximately a 25 μs loop. This allows the joint position controller 304 to service all robotic arm current controllers, such as the remote current controller 610 and/or the current controller 402-1, during each of its process cycles (i.e., until it receives a next set of joint position commands "$\hat{\theta}_C$"). It also allows the remote current controller 610 to receive position data from its distal sensor processing units (e.g., 612-3, 612-4) and generate motor control signals (e.g., 621-3, 621-4) for each of its controlled motors (e.g., 401-3, 401-4) during each of its process cycles (i.e., until it receives a next set of current commands "$\hat{I}_C$").

The remote current controller 610 provides a set of pulse-width modulated current signals to each of its controlled motors (e.g., 401-3, 401-4) over individual signal lines (e.g., sets of signal lines 621-3, 621-4). Typically, each set of signal lines includes three voltage/current lines for connection to corresponding windings of a three-phase brushless DC motor. Current and/or voltage sensors are preferably included in the remote current controller 610 to sense currents being drawn through and/or voltages being applied on each signal line. The sensed currents may be used in a conventional manner for current control purposes in the remote current controller 610.

In addition to the first and second arrangements, 500 and 600, of networked motor control systems as described herein, hybrid arrangements which combine aspects of the first and second arrangements may also be employed in the medical robotic system 1000. Such hybrid systems allow use of aspects of the first arrangement 500 when those aspects are more advantageous than aspects of the second arrangement 600, and vice versa. For example, aspects of the first arrangement 500 may be advantageous for implementation purposes when space and heating concerns are minimal. On the other hand, aspects of the second arrangement 600 may be advantageous when space and heating are of particular concern.

Referring back to FIG. 3, the manipulator 200 includes a hybrid arrangement of networked motor control systems. The hybrid arrangement combines aspects of the first arrangement 500 of FIG. 7 with aspects of the second arrangement 600 of FIG. 8.

The first arrangement 500 of FIG. 7 is used for pitch and yaw control of the manipulator 200. In particular, a yaw current controller (e.g., 402-1) and its corresponding transmitter/receiver (e.g., 404-1) are provided on the printed circuit board 730 to control the yaw motor 221 (e.g., 401-1) using feedback from yaw sensor processing unit 721 (e.g., 403-1). A pitch current controller (e.g., 402-2) and its corresponding transmitter/receiver (e.g., 404-2) are also provided on the printed circuit board 730 to control the pitch motor 222 (e.g., 401-2) using feedback from a pitch sensor processing unit 722 (e.g., 403-2). In this example, the joint position controller 304 may be disposed, wholly or partially in a distributed manner, in the base 120' of the patient side cart 110'. Alternatively, it may be disposed, wholly or partially in a distributed manner, in other parts of the medical robotic system 1000, such as in the vision cart 170 and surgeon console 100. Further, since the yaw and current controllers (e.g., 402-1 and 402-2) are disposed on the same printed circuit board, they may also share the same transmitter/receiver rather than having their own individual transmitter/receiver.

It may be advantageous for the pitch and yaw current controllers to be proximate to their respective motors for implementation purposes. On the other hand, placing them in link 201 presents very little problem with space requirements, because link 201 is relatively large and can easily accommodate the printed circuit board 730. Also, heat generated by the pitch and yaw controllers presents no problems by placing them in link 201 since this link is at the proximal end of the manipulator 200. Therefore, link 201 is further away from a patient who is being treated at the time than the more distal links 202, 203, and 204. Further, since link 201 is relatively large compared to the more distal links 202, 203, and 204, it has more internal volume and external surface area to dissipate any heat generated by the pitch and yaw current controllers housed by the link.

In contrast, the I/O motor 223 is disposed at a distal end of the link 204. Since this location is close to the patient and restricted in space, locating its current controller near the motor 223 would present a heating problem. Further, motors 224 which actuate corresponding degrees of freedom of the medical device 250 are housed in the carriage 262. Since the interior of the carriage 262 is especially restricted in space and further, since the carriage 262 may move towards the distal end of the link 204 so as to be near the patient, housing the current controllers for motors 224 in the carriage 262 may also present heating problems which may result in harming the patient or reducing the operational life of components.

Thus, it is desirable to house the current controller for motor 223 in a different housing than the link 204. Also, it is desirable to house the current controllers for motors 224 in a different housing than the carriage 262. In contrast, it is desirable to house the distal sensor processing units (e.g., 612-3, 612-4) in the same housing as their respective motors, because their sensors should be near the motors to sense their rotor angles. Also, the heat generated by their transmitter/receiver units (e.g. 611-3, 611-4) is relatively small compared to the heat generated by operation of the remote current controller 610.

Aspects of the second arrangement 600 of FIG. 8 may therefore be applied so that a remote current controller (e.g., 610) may be implemented for current control of motors 223 and 224. In this case, however, rather than having the transmitter/receiver 615 of the remote current controller 610 communicating directly with the joint position controller 304, such as shown in FIG. 6, it communicates directly instead with the transmitter/receiver (e.g., 404-2) of the yaw current controller (e.g., 402-2) on the printed circuit board 730 via communication link 503, such as shown in FIGS. 7 and 9, in the daisy chain network.

Figure 9:
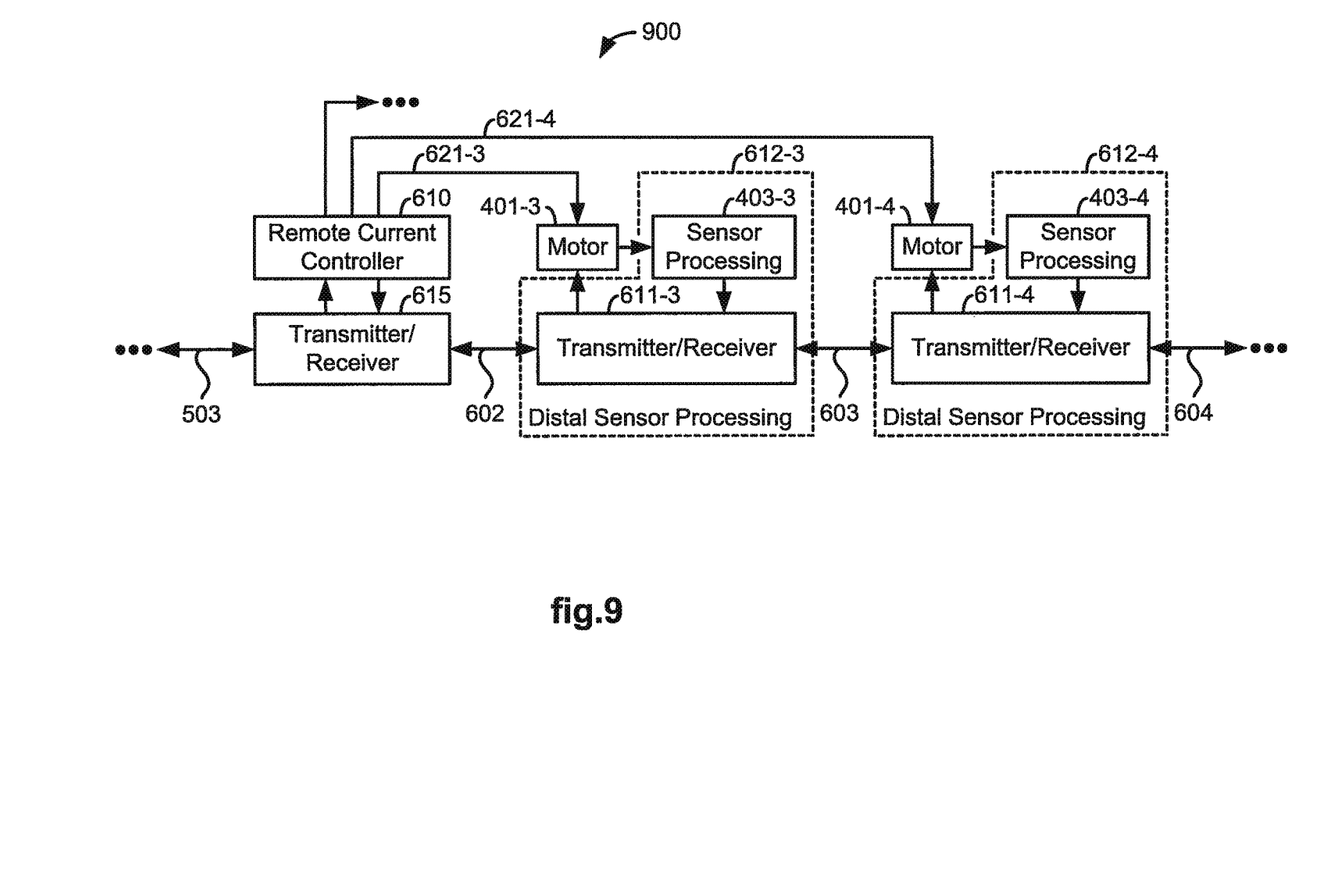
FIG. 9 illustrates a block diagram of a portion of a hybrid arrangement of networked motor control systems included in a medical robotic system.

To implement the arrangement 900 of FIG. 9, the remote current controller 610, which provides current control for motors 223 and 224, is provided along with its transmitter/receiver 615 on printed circuit board 740 which is housed in link 202. This is a preferable housing for the remote current controller 610, because link 202 is a larger housing than the link 204 and it is especially larger than the carriage 262, so that heat generated by it has more internal volume and external surface area to dissipate. Also, link 202 is further away from the patient. Therefore, any heat generated within link 202 is less likely to cause discomfort or harm to the patient. The distal sensor processing unit (e.g., 612-3) for the I/O motor 223 is provided by sensors 723 in close proximity to motor 223 with processing and communications performed on a printed circuit board 750. Also, distal sensor processing units for the motors 224 are provided by sensors in close proximity to the motors 224 with processing and communications performed on printed circuit boards 724 in the carriage 262, so that they are also in close proximity to their respective motors 224. Thus, in this example, the joint position controller 304 is housed in a proximal housing, such as the base 120' of the patient side cart 110'. The distal sensor processing units 612-3, 612-4 are housed in distal housings, such as the link 204 and carriage 262. The remote current controller 610 and its transmitter/receiver 615 are housed in an intermediate housing (i.e., a housing between the proximal and distal housings), such as the link 202.

Although the various aspects of the present invention have been described with respect to a preferred embodiment, it will be understood that the invention is entitled to full protection within the full scope of the appended claims.

We claim:

1. A distributed control system for controlling a plurality of motors to actuate movement of a robotically manipulated device, the distributed control system comprising:
   a plurality of sensors coupled to the plurality of motors for sensing states of the plurality of motors, wherein the plurality of sensors and the plurality of motors are disposed in one or more distal housings; and
   a remote current controller adapted to receive commands indicative of commanded positions of the plurality of motors from a position controller, receive information of the sensed states of the plurality of motors, generate individual motor driving signals for the plurality of motors by using the received commands and the received information of the sensed states of the plurality of motors, and provide the individual motor driving signals to the plurality of motors;
   wherein the position controller is disposed in a proximal housing, and wherein the remote current controller is disposed in an intermediate housing that is between the proximal housing and the one or more distal housings.

2. The distributed control system according to claim 1, wherein the information of the sensed states of the plurality of motors comprises information of rotor angles of the plurality of motors.

3. The distributed control system according to claim 1, wherein the robotically manipulated device is an instrument, and wherein the plurality of motors moves the instrument in corresponding degrees of freedom.

4. The distributed control system according to claim 3, wherein the instrument has a shaft, a distal tip, and a wrist mechanism coupling the distal tip to the shaft, and wherein the plurality of motors comprises one or more motors for actuating corresponding degrees of freedom of the wrist mechanism.

5. The distributed control system according to claim 3, wherein the instrument has an end effector, and wherein the plurality of motors comprises one or more motors for actuating corresponding degrees of freedom of the end effector.

6. The distributed control system according to claim 1, wherein the robotically manipulated device is manipulated by a robotic arm, wherein the robotic arm comprises a plurality of links and a plurality of joints, wherein each of the plurality of links is enclosed by a housing, and wherein the intermediate housing and the one or more distal housings enclose corresponding ones of the plurality of links.

7. The distributed control system according to claim 6, wherein the robotic arm is mounted to a base structure, and wherein the base structure comprises the proximal housing.

8. The distributed control system according to claim 1, wherein the remote current controller communicates with the plurality of sensors through a plurality of communication links included in a daisy chain network, and wherein the position controller communicates with the remote controller through a proximal communication link in the daisy chain network.

9. The distributed control system according to claim 8, wherein the daisy chain network comprises a packet-based network.

10. The distributed control system according to claim 1, wherein the plurality of motors comprises one or more brushless DC motors, and wherein the motor driving signals are pulse-width modulated current signals.

11. A robotic system comprising:
one or more distal housings in which a plurality of motors and a plurality of sensors are housed, wherein the plurality of sensors is coupled to the plurality of motors for sensing states of the plurality of motors;
a proximal housing in which a position controller is housed, wherein the position controller generates commands indicative of commanded positions of the plurality of motors; and
an intermediate housing in which a remote current controller is housed, wherein the intermediate housing is between the proximal housing and the one or more distal housings, and wherein the remote current controller is adapted to: receive the commands, receive information of the sensed states of the plurality of motors, generate individual motor driving signals for the plurality of motors using the received commands and the received information of the sensed states of the plurality of motors, and provide the individual motor driving signals to the plurality of motors over individual signal lines.

12. The robotic system according to claim 11, wherein the information of the sensed states of the plurality of motors comprises information of rotor angles of the plurality of motors.

13. The robotic system according to claim 11, further comprising:
an instrument;
wherein the plurality of motors moves the instrument in corresponding degrees of freedom.

14. The robotic system according to claim 13, wherein the instrument has a shaft, a distal tip, and a wrist mechanism coupling the distal tip to the shaft, and wherein the plurality of motors comprises one or more motors for actuating corresponding degrees of freedom of the wrist mechanism.

15. The robotic system according to claim 13, wherein the instrument has an end effector, and wherein the plurality of motors comprises one or more motors for actuating corresponding degrees of freedom of the end effector.

16. The robotic system according to claim 11, wherein the instrument is manipulated by a robotic arm, wherein the robotic arm comprises a plurality of links and a plurality of joints, wherein each of the plurality of links is enclosed by a housing, and wherein the intermediate housing and the one or more distal housings enclose corresponding ones of the plurality of links.

17. The robotic system according to claim 16, wherein the robotic arm is mounted to a base structure, and wherein the base structure comprises the proximal housing.

18. The robotic system according to claim 11, wherein the remote current controller communicates with the plurality of sensors through a plurality of communication links included in a daisy chain network, and wherein the position controller communicates with the remote controller through a proximal communication link in the daisy chain network.

19. The robotic system according to claim 18, wherein the daisy chain network comprises a packet-based network.

20. The robotic system according to claim 11, wherein the plurality of motors comprises one or more brushless DC motors, and wherein the motor driving signals are pulse-width modulated current signals.

* * * * *